US012145853B2

(12) United States Patent
Colbeau-Justin et al.

(10) Patent No.: US 12,145,853 B2
(45) Date of Patent: Nov. 19, 2024

(54) PRECIPITATED SILICA AND PROCESS FOR ITS MANUFACTURE

(71) Applicant: RHODIA OPERATIONS, Aubervilliers (FR)

(72) Inventors: Frédéric Colbeau-Justin, Collonges au Mont d'Or (FR); Emmanuelle Allain Najman, L'Hay les Roses (FR); Pascaline Lauriol-Garbey, Saint-Cyr-au-Mont-d'Or (FR)

(73) Assignee: RHODIA OPERATIONS, Lyons (FR)

( * ) Notice: Subject to any disclaimer, the term of this patent is extended or adjusted under 35 U.S.C. 154(b) by 672 days.

(21) Appl. No.: 17/291,027

(22) PCT Filed: Nov. 6, 2019

(86) PCT No.: PCT/EP2019/080392
§ 371 (c)(1),
(2) Date: May 4, 2021

(87) PCT Pub. No.: WO2020/094714
PCT Pub. Date: May 14, 2020

(65) Prior Publication Data
US 2021/0387858 A1 Dec. 16, 2021

(30) Foreign Application Priority Data
Nov. 8, 2018 (EP) .................................... 18306461

(51) Int. Cl.
| B01J 21/08 | (2006.01) |
| A61L 15/18 | (2006.01) |
| B01J 20/10 | (2006.01) |
| C01B 33/193 | (2006.01) |
| C08K 3/36 | (2006.01) |
| B60C 1/00 | (2006.01) |

(52) U.S. Cl.
CPC ............ *C01B 33/193* (2013.01); *A61L 15/18* (2013.01); *B01J 20/103* (2013.01); *B01J 21/08* (2013.01); *C08K 3/36* (2013.01); *B60C 1/00* (2013.01); *C01P 2004/51* (2013.01); *C01P 2006/12* (2013.01); *C01P 2006/80* (2013.01); *C08K 2201/006* (2013.01)

(58) Field of Classification Search
CPC .......... B01J 21/08; B01J 20/103; C08K 3/36; A61L 15/18; C01B 33/193
See application file for complete search history.

(56) References Cited

U.S. PATENT DOCUMENTS

| 7,070,749 | B2 | 7/2006 | Linder et al. | |
| 7,135,429 | B2* | 11/2006 | Raman | B01J 20/103 |
| | | | | 502/238 |
| RE40,299 | E * | 5/2008 | Bruinsma | B01J 20/103 |
| | | | | 423/335 |
| 7,790,138 | B2* | 9/2010 | Schimanski | B01J 21/08 |
| | | | | 106/446 |
| 8,183,173 | B2* | 5/2012 | McDaniel | B01J 21/08 |
| | | | | 502/256 |
| 8,273,804 | B2* | 9/2012 | Nishimura | C08L 7/00 |
| | | | | 152/905 |
| 8,647,599 | B2* | 2/2014 | Schimanski | C01G 23/04 |
| | | | | 502/232 |
| 9,943,826 | B2* | 4/2018 | Haynes | B01J 35/1047 |
| 11,111,360 | B2* | 9/2021 | Pawlak | C08K 3/06 |
| 11,628,420 | B2* | 4/2023 | Grothe | B01J 37/033 |
| | | | | 502/242 |
| 2002/0061404 | A1 | 5/2002 | Schubert et al. | |
| 2002/0112647 | A1 | 8/2002 | Linder et al. | |
| 2011/0263784 | A1* | 10/2011 | Valero | C01B 33/193 |
| | | | | 524/521 |
| 2011/0294936 | A1* | 12/2011 | Sato | C08K 5/101 |
| | | | | 524/315 |
| 2013/0178569 | A1* | 7/2013 | Guy | C08K 3/36 |
| | | | | 106/483 |
| 2015/0266742 | A1 | 9/2015 | Clouin et al. | |
| 2015/0284546 | A1 | 10/2015 | Guy et al. | |
| 2017/0015807 | A1* | 1/2017 | Boivin | C09C 1/3072 |
| 2017/0058111 | A1* | 3/2017 | Boivin | C01B 33/193 |

(Continued)

FOREIGN PATENT DOCUMENTS

| FR | 2997405 A1 | 5/2014 |
| WO | 2013092745 A1 | 12/2011 |

OTHER PUBLICATIONS

Shannon R D, Revised effective ionic radii and systematic studies of interatomic distances in halides and chalcogenides, (1976) Acta crystallographica. Section a, foundations of crystallography, 19760901 Munksgaard, Copenhagen, DK, vol. A32, Nr: Part 05, pp. 751-767, XP001085186.

(Continued)

*Primary Examiner* — Cam N. Nguyen
(74) *Attorney, Agent, or Firm* — Osha Bergman Watanabe & Burton LLP

(57) ABSTRACT

Precipitated silica having large median particle size for use as reinforcing filler in elastomeric compositions as well as its method of manufacture. In particular, a precipitated silica characterised by a CTAB surface area $S_{CTAB}$ in the range from 70 to 350 m²/g; an amount $W_M$ of at least one metal M selected from elements of groups 3, 4 and 5 of at least 0.1 mol %; and a median particle size d50, measured by centrifugal sedimentation, such that: $|d50| \geq 183 \times |R_{ION}| \times |W_M| - 0.67 \times |S_{CTAB}| + 233$ (I) wherein $|d50|$ represents the numerical value of median particle size d50 measured by centrifugal sedimentation and expressed in nm; $|R_{ION}|$, the numerical value of the ionic radius of metal M expressed in nm; $|S_{CTAB}|$, the numerical value of the CTAB surface area $S_{CTAB}$ expressed in m²/g; and $|W_M|$, the numerical value of the percentage molar amount of the metal $W_M$.

16 Claims, No Drawings

(56) References Cited

U.S. PATENT DOCUMENTS

2017/0073238 A1* 3/2017 Guy .................. C01B 33/193
2020/0079654 A1* 3/2020 Allain Najman .... B01J 35/1014

OTHER PUBLICATIONS

Standard NF ISO 5794-1, 2010, Appendix G Rubber compounding ingredients—Silica, precipitated, hydrated—Part 1: Non-rubber tests p. 36.
Standard NF ISO 5794-1, 2010, Appendix E (Jun. 2010) Rubber compounding ingredients—Silica, precipitated, hydrated—Part 1: Non-rubber tests.
NF ISO 37 standard (Nov. 2017) Rubber, vulcanized or thermoplastic—Determination of tensile stress-strain properties.

* cited by examiner

PRECIPITATED SILICA AND PROCESS FOR ITS MANUFACTURE

CROSS-REFERENCE TO RELATED APPLICATIONS

This application is a U.S. national stage entry under 35 U.S.C. § 371 of International Application No. PCT/EP2019/080392 filed Nov. 6, 2019, which claims priority to European patent application No. 18306461.7, filed on Nov. 8, 2018, the whole content of this application being incorporated herein by reference for all purposes.

TECHNICAL FIELD

The present invention relates to precipitated silica and to a process for its manufacture.

BACKGROUND ART

The use of precipitated silica as a reinforcing filler in polymeric compositions is known. In particular it is known to use precipitated silica as reinforcing filler in elastomeric compositions. Such use is highly demanding: the filler has to readily and efficiently incorporate and disperse in the elastomeric composition and, typically in conjunction with a coupling reagent, enter into a chemical bond with the elastomer(s), to lead to a high and homogeneous reinforcement of the elastomeric composition. In general, precipitated silica is used in order to improve the mechanical properties of the elastomeric composition as well as abrasion performance. Indeed there is always the need of precipitated silica capable of providing a balance between conflicting properties such as abrasion resistance and/or polymer reinforcement on one hand and reduced energy dissipation properties, which in turn provide for reduced heat build-up, on the other.

SUMMARY OF INVENTION

A first objective of the present invention is to provide novel precipitated silica which, when incorporated efficiently into polymeric compositions, provides an improved balance of performance properties. A second objective of the invention is a process for the manufacture of the precipitated silica. A further objective of the invention is to provide elastomeric compositions comprising the precipitated silica as reinforcing filler. These objectives are achieved by the inventive precipitated silica defined in detail in the description which follows and in the claims and the examples.

It has been found that good mechanical properties and reduced energy dissipation (hence heat build-up) in elastomeric compositions can be obtained by the use of a precipitated silica containing at least one metal M selected from the group consisting of the elements of groups 3, 4 and 5 in an amount of at least 0.1 mol % and having a large a median particle size. d50, measured by centrifugal sedimentation, with respect to its CTAB surface area.

Precipitated silica containing transition metals (e.g. Ti, Zr, V, Sc) has been previously described, for instance in U.S. Pat. No. 7,070,749, which discloses foreign-atom-doped precipitated silicas suitable for use in papermaking applications. U.S. Pat. No. 7,070,749 does not disclose the size of the silica particles measured by means of centrifugal sedimentation in a disc centrifuge.

FR2997405 discloses compositions comprising a Ti-doped precipitated silica in combination with selected phosphinate/phosphonate coupling agents. The size of the particles of the precipitated silica disclosed in FR2997405 does not meet the criterion expressed by formula (I) hereunder.

DESCRIPTION OF INVENTION

The precipitated silica of the invention is characterised by:
- a CTAB surface area $S_{CTAB}$ in the range from 70 to 350 m$^2$/g;
- an amount $W_M$ of at least one metal M, selected from the group consisting of the elements of groups 3, 4 and 5, of at least 0.1 mol %; and
- a median particle size d50, measured by centrifugal sedimentation, such that (I):

$$|d50| \geq 183 \times |R_{ION}| \times |W_M| - 0.67 \times |S_{CTAB}| + 233 \qquad (I)$$

wherein:
|d50| represents the numerical value of the median particle size d50 measured by centrifugal sedimentation and expressed in nm; $|R_{ION}|$ represents the numerical value of the ionic radius of the metal M expressed in nm; $|S_{CTAB}|$ represents the numerical value of the CTAB surface area $S_{CTAB}$ expressed in m$^2$/g; and $|W_M|$ represents the numerical value of the percentage molar amount $W_M$ of metal M.

In the present specification, the terms "silica" and "precipitated silica" are used as synonyms.

In the present specification numerical ranges defined by the expression "from a to b" indicate a numerical range which includes end values a and b.

Numerical ranges defined by the expression "a is at least b" indicate ranges wherein a is equal to or greater than b.

For the avoidance of doubts, the symbol "×" in equation (I) represents the multiplication sign, such that the expression "a×b" means a multiplied by b.

The CTAB surface area $S_{CTAB}$ is a measure of the external specific surface area as determined by measuring the quantity of N hexadecyl-N,N,N-trimethylammonium bromide adsorbed on the silica surface at a given pH.

The CTAB surface area $S_{CTAB}$ is at least 70 m$^2$/g, typically at least 80 m$^2$/g, even at least 90 m$^2$/g. The CTAB surface area $S_{CTAB}$ may be greater than 100 m$^2$/g. The CTAB surface area $S_{CTAB}$ may even be greater than 120 m$^2$/g, greater than 140 m$^2$/g, possibly even greater than 150 m$^2$/g.

The CTAB surface area does not exceed 350 m$^2$/g, typically it does not exceed 320 m$^2$/g. The CTAB surface area $S_{CTAB}$ may be lower than 300 m$^2$/g.

For elastomer reinforcement applications advantageous ranges of CTAB surface area $S_{CTAB}$ are: from 70 to 300 m$^2$/g, from 80 to 300 m$^2$/g, from 120 to 300 m$^2$/g, from 140 to 300 m$^2$/g, even from 145 to 300 m$^2$/g, still from 130 to 280 m$^2$/g.

The BET surface area $S_{BET}$ of the inventive silica is not particularly limited. BET surface area $S_{BET}$ is generally at least 80 m$^2$/g, at least 100 m$^2$/g, at least 140 m$^2$/g, at least 160 m$^2$/g, even at least 170 m$^2$/g, at least 180 m$^2$/g, and even at least 200 m$^2$/g. The BET surface area $S_{BET}$ can be as high as 400 m$^2$/g, even as high as 450 m$^2$/g.

The inventive silica contains at least one metal M selected from the group consisting of the elements of group 3, 4 and 5 according to IUPAC nomenclature. For the avoidance of doubts group 3 is considered herein as consisting of the following elements: Sc, Y, La and Ac.

Metal M is preferably selected from the group consisting of Sc, Y, Ti, Zr, Hf, V, Nb and Ta. More preferably metal M is selected from the group consisting of Sc, Y, Ti, Zr and Hf.

Advantageously metal M is selected from the group consisting of Y, Ti and Zr. Metal M may advantageously be Zr.

Metal M is present in an amount $W_M$ of at least 0.1 mol %. Throughout the present text the amount of metal M, $W_M$, is defined as the amount of the at least one element M by moles with respect to the moles of silica.

$W_M$ is preferably at least 0.2 mol %, even at least 0.3 mol %. Advantageously, $W_M$ is in the range from 0.1 to 7.0 mol %, typically from 0.2 to 5.0 mol %, even from 0.3 to 3.0 mol %.

When metal M is Zr, $W_M$ may conveniently be in the range from 0.2 to 3.5 mol %, even from 0.3 to 3.0 mol %, still from 0.4 to 2.5 mol %.

It has to be understood that the inventive silica may contain other elements in addition to metal M, notable, non-limiting examples are for instance Mg, Ca, Al or Zn.

An important feature of the inventive silica is the large median particle size (particle diameter) d50 for a given $S_{CTAB}$ value. In particular, it has been found that the median particle size of the inventive silica increases with the amount of metal M in the silica and its ionic radius.

It has been found that the median particle size d50 of the inventive silica is correlated to the amount of metal M, $W_M$, its ionic radius, $R_{ION}$, and the CTAB surface area $S_{CTAB}$ by equation (I):

$$|d50| \geq 183 \times |R_{ION}| \times |W_M| - 0.67 \times |S_{CTAB}| + 233 \quad (I).$$

In equation (I), |d50| represents the numerical value of the median particle size d50 measured by centrifugal sedimentation and expressed in nm. |d50| is an adimensional number. As an example if the value of d50 measured by centrifugal sedimentation is 100 nm, |d50| is 100.

In equation (I), $|R_{ION}|$ represents the value of the ionic radius of metal M, expressed in nm, in its most representative higher coordination number and oxidation state. As an example if the ionic radius is 0.072 nm, $|R_{ION}|$ is 0.072.

The values of the ionic radius were taken from R. D. Shannon, *"Revised Effective Ionic Radii and Systematic Studies of Interatomic Distances in Halides and Chalcogenides"*, Acta Crystallographica, A32, 751-767 (1976) and are reported in Table 1.

TABLE 1

| Metal M (oxidation state, coordination number) | $R_{ION}$ (nm) |
|---|---|
| Sc (III, 8) | 0.084 |
| Y (III, 8) | 0.102 |
| La (III, 8) | 0.116 |
| Ac (III, 6) | 0.112 |
| Ti (IV, 6) | 0.060 |
| Zr (IV, 6) | 0.072 |
| Hf (IV, 6) | 0.072 |
| V (V, 5) | 0.046 |
| Ta (V, 8) | 0.074 |
| Nb (V, 8) | 0.074 |

In equation (I), the numerical value of the percentage amount of metal M, $W_M$, $|W_M|$ is an adimensional number. As an example if the amount of metal M with respect to the weight of silica is 0.3 mol %, then $|W_M|$ is 0.3.

When more than one metal M is present in the precipitated silica, the value of $|R_{ION}| \times |W_M|$ in (I) corresponds to the sum of $|R_{ION}| \times |W_M|$ for each metal.

In equation (I), $|S_{CTAB}|$ represents the numerical value of the CTAB surface area $S_{CTAB}$ expressed in m²/g. $|S_{CTAB}|$ is an adimensional number. As an example if the measured value of $S_{CTAB}$ is 200 m²/g, $|S_{CTAB}|$ is 200.

In the CTAB surface area $S_{CTAB}$ range from 70 to 350 m²/g, the inventive silica is characterised by a median particle size d50 which is generally greater than 30 nm, even greater than 50 nm.

The d50 value of the inventive silica typically does not exceed 300 nm, more typically it does not exceed 250 nm.

The precipitated silica of the invention is generally characterised by a broad particle size distribution. The term "particle" is used herein to refer to aggregates of primary silica particles. The term particle is used to refer to the smallest aggregate of primary silica particles that can be broken by mechanical action. In other words, the term particle refers to an assembly of indivisible primary particles.

Parameter Ld, determined by means of centrifugal sedimentation in a disc centrifuge as detailed hereafter, is used to characterize the width of the particle size distribution. Ld is defined as follows:

$$Ld=(d84-d16)/d50$$

wherein dn is the particle diameter below which one finds n % of the total measured mass. Ld is an adimensional number. The width of the particle size distribution Ld is calculated on the cumulative particle size curve. As an example, d50 represents the particle diameter below (and above) which 50% of the total mass of particles is found. Thus, d50 represents the median particle size of a given distribution, wherein the term "size" in this context has to be intended as "diameter".

The width of the particle size distribution Ld is at least 1.2, typically at least 1.4, even at least 1.5. The width of the particle size distribution Ld is no more than 4.0, typically no more than 3.5.

Advantageously, the width of the particle size distribution Ld of the inventive silica may be in the range from 1.2 to 3.5, even in the range from 1.4 to 3.0. The width of the particle size distribution Ld of the inventive silica can be in the range from 1.5 to 2.8, preferably from 1.6 to 2.5.

A second object of the present invention is a process for preparing the inventive precipitated silica, said process comprising:

(i) providing a starting solution having a pH from 2.00 to 5.00, (ii) simultaneously adding a silicate and an acid to said starting solution such that the pH of the reaction medium is maintained in the range from 2.00 to 5.00, (iii) stopping the addition of the acid and of the silicate and adding a base to the reaction medium to raise the pH of said reaction medium to a value from 7.00 to 10.00, (iv) simultaneously adding to the reaction medium a compound of at least one metal M, a silicate and an acid, such that the pH of the reaction medium is maintained in the range from 7.00 to 10.00, (v) stopping the addition of the silicate and of the compound of the at least one metal M while continuing the addition of the acid to the reaction medium to reach a pH of the reaction medium of less than 6.00 and obtaining a suspension of precipitated silica.

The term "base" is used herein to refer to one or more than one base which can be added during the course of the inventive process and it includes the group consisting of silicates as defined hereafter. Any base may be used in the process. In addition to silicates, notable non-limiting examples of suitable bases are for instance alkali metal hydroxides and ammonia.

The term "silicate" is used herein to refer to one or more than one silicate which can be added during the course of the inventive process. The silicate is typically selected from the group consisting of the alkali metal silicates. The silicate is advantageously selected from the group consisting of sodium and potassium silicate. The silicate may be in any known form, such as metasilicate or disilicate.

In the case where sodium silicate is used, the latter generally has an $SiO_2/Na_2O$ weight ratio of from 2.0 to 4.0, in particular from 2.4 to 3.9, for example from 3.1 to 3.8.

The silicate may have a concentration (expressed in terms of $SiO_2$) of from 3.9 wt % to 25.0 wt %, for example from 5.6 wt % to 23.0 wt %, in particular from 5.6 wt % to 20.7 wt %.

The term "acid" is used herein to refer to one or more than one acid which can be added during the course of the inventive process. Any acid may be used in the process. Use is generally made of a mineral acid, such as sulfuric acid, nitric acid, phosphoric acid or hydrochloric acid, or of an organic acid, such as carboxylic acids, e.g. acetic acid, formic acid or carbonic acid.

The acid may be metered into the reaction medium in diluted or concentrated form. The same acid at different concentrations may be used in different stages of the process. Preferably the acid is sulfuric acid.

In a preferred embodiment of the process sulfuric acid and sodium silicate are used in all of the stages of the process. Preferably, the same sodium silicate, that is sodium silicate having the same concentration expressed as $SiO_2$, is used in all of the stages of the process.

In step (i) of the process a starting solution having a pH from 2.00 to 5.00 is provided in the reaction vessel. The starting solution is an aqueous solution, the term "aqueous" indicating that the solvent is water.

Preferably, the starting solution has a pH from 2.50 to 5.00, especially from 3.00 to 4.50; for example, from 3.50 to 4.50.

The starting solution may be obtained by adding an acid to water so as to obtain a pH value as detailed above.

Alternatively, the starting solution may contain a silicate. In such a case it may be obtained by adding acid to a mixture of water and silicate to obtain a pH from 2.00 to 5.00.

The starting solution may also be prepared by adding acid to a solution containing preformed silica particles at a pH below 7.00, so as to obtain a pH value from 2.00 to 5.00, preferably from 2.50 to 5.00, especially from 3.00 to 4.50, for example from 3.50 to 4.50.

The starting solution of step (i) may or may not comprise an electrolyte. Preferably, the starting solution of step (i) contains an electrolyte.

The term "electrolyte" is used herein in its generally accepted meaning, i.e. to identify any ionic or molecular substance which, when in solution, decomposes or dissociates to form ions or charged particles. The term "electrolyte" is used herein to indicate one or more than one electrolyte may be present. Mention may be made of electrolytes such as the salts of alkali metals and alkaline-earth metals. Advantageously, the electrolyte for use in the starting solution is the salt of the metal of the starting silicate and of the acid used in the process. Notable examples are for example sodium chloride, in the case of the reaction of a sodium silicate with hydrochloric acid or, preferably, sodium sulfate, in the case of the reaction of a sodium silicate with sulfuric acid.

Preferably, when sodium sulfate is used as electrolyte in step (i), its concentration in the starting solution is from 8 to 40 g/L, especially from 10 to 35 g/L, for example from 13 to 30 g/L.

Step (ii) of the process comprises a simultaneous addition of an acid and of a silicate to the starting solution. The rates of addition of the acid and of the silicate during step (ii) are controlled in such a way that the pH of the reaction medium is maintained in the range from 2.00 to 5.00. The pH of the reaction medium is preferably maintained in the range from 2.50 to 5.00, especially from 3.00 to 5.00, for example from 3.20 to 4.80.

The simultaneous addition in step (ii) is advantageously performed in such a manner that the pH value of the reaction medium is always equal (to within ±0.20 pH units) to the pH reached at the end of step (i).

Preferably, step (ii) consists of a simultaneous addition of acid and silicate as detailed above.

In one embodiment of the inventive process, an intermediate step (ii') may be carried out between step (i) and step (ii), wherein a silicate and an acid are added to the starting solution such that the pH of the reaction medium is maintained in the range from 2.00 to 9.50. The addition of silicate and acid can be simultaneous for all or for only a part of step (ii'). Step (ii') is typically protracted for 1 to 10 minutes, preferable for 2 to 8 minutes before step (ii) is initiated.

Next, in step (iii), the addition of the acid and of the silicate is stopped and a base is added to the reaction medium. The addition of the base is stopped when the pH of the reaction medium has reached a value of from 7.00 to 10.00, preferably from 7.50 to 9.50.

In a first embodiment of the process the base is a silicate. Thus, in step (iii), the addition of the acid is stopped while the addition of the silicate to the reaction medium is continued until a pH of from 7.00 to 10.00, preferably from 7.50 to 9.50, is reached.

In a second embodiment of the process the base is different from a silicate and it is selected from the group consisting of the alkali metal hydroxides, preferably sodium or potassium hydroxide. When sodium silicate is used in the process a preferred base may be sodium hydroxide.

Thus, in this second embodiment of the process, in step (iii), the addition of the acid and of the silicate is stopped and a base, different from a silicate, is added to the reaction medium until a pH of from 7.00 to 10.00, preferably from 7.50 to 9.50, is reached.

At the end of step (iii), that is after stopping the addition of the base, it may be advantageous to perform a maturing step of the reaction medium. This step is preferably carried out at the pH obtained at the end of step (iii). The maturing step may be carried out while stirring the reaction medium. The maturing step is preferably carried out under stirring of the reaction medium over a period of 2 to 45 minutes, in particular from 5 to 25 minutes. Preferably the maturing step does not comprise any addition of acid or silicate.

After step (iii) and the optional maturing step, a simultaneous addition of a compound at least one metal M, of an acid and of a silicate is performed, such that the pH of the reaction medium is maintained in the range from 7.00 to 10.00, preferably from 7.50 to 9.50.

The simultaneous addition of a compound of at least one metal M, of an acid and of a silicate (step (iv)) is typically performed in such a manner that the pH value of the reaction medium is maintained equal to the pH reached at the end of the preceding step (to within ±0.20 pH units), step (iii).

It should be noted that the inventive process may comprise additional steps. For example, between step (iii) and step (iv), and in particular between the optional maturing step following step (iii) and step (iv), an acid can be added to the reaction medium. The pH of the reaction medium after this addition of acid should remain in the range from 7.00 to 9.50, preferably from 7.50 to 9.50.

In step (v), the addition of the silicate and of the compound of at least one metal M is stopped while continuing the addition of the acid to the reaction medium so as to obtain a pH value in the reaction medium of less than 6.00, preferably from 3.00 to 5.50, in particular from 3.00 to 5.00. A suspension of precipitated silica is obtained in the reaction vessel.

At the end of step (v), and thus after stopping the addition of the acid to the reaction medium, a maturing step may advantageously be carried out. This maturing step may be carried out at the same pH obtained at the end of step (v) and under the same time conditions as those described above for the maturing step which may be optionally carried out between step (iii) and (iv) of the process.

A compound of at least one metal M is metered into the reaction medium during step (iv), that is during the simultaneous addition of an acid and of a silicate to the reaction medium at a pH in the range from 7.00 to 10.00. The compound of at least one metal M may be metered to the reaction medium over the whole duration of step (iv), that is at the same time as the addition of acid and silicate. Alternatively, it may be metered during only one part of step (iv), for instance only after a first simultaneous addition of acid and silicate has taken place. The compound of at least one metal M is typically added into the reaction medium in the form of a solution, typically an aqueous solution. All of the compound of at least one metal M is added during step (iv).

Any compound of metal M may be used in the process of the invention provided it is soluble in water, and in particular soluble at a pH in the range from 7.00 to 10.00. Notable examples of suitable compounds include but are not limited to chlorides, sulfates, oxysulfates, or nitrates of metal M. The compound is generally selected from the group consisting of the sulfates or oxysulfates. The compound of metal M is generally added to the reaction medium in the form of a solution, typically an aqueous solution.

The amount of the compound of at least one metal M added to the reaction medium during step (iv) is calculated so that the amount of metal M, $W_M$, in the final product is at least 0.1 mol %.

The reaction vessel in which the entire reaction of the silicate with the acid is performed is usually equipped with adequate stirring and heating equipment.

The entire reaction of the silicate with the acid (steps (i) to (v)) is generally performed at a temperature from 40 to 97° C., in particular from 60 to 95° C., preferably from 80 to 95° C., more preferably from 85 to 95° C.

According to one variant of the invention, the entire reaction of the silicate with the acid is performed at a constant temperature, usually of from 40 to 97° C., in particular from 80 to 95° C., and even from 85 to 95° C.

According to another variant of the invention, the temperature at the end of the reaction is higher than the temperature at the start of the reaction: thus, the temperature at the start of the reaction (for example during steps (i) to (iii)) is preferably maintained in the range from 40 to 85° C. and the temperature is then increased, preferably up to a value in the range from 80 to 95° C., even from 85 to 95° C., at which value it is maintained (for example during steps (iv) and (v)), up to the end of the reaction.

The different parameters of the process, e.g. temperature, pH of the reaction medium, amount of electrolyte present in step (i), amount of the compound of at least one metal M can be varied to obtain precipitated silica having the required value of CTAB specific surface and amount of metal M.

At the end of the steps that have just been described, a suspension of precipitated silica is obtained, which is subsequently separated (liquid/solid separation). The process typically comprises a further step (vi) of filtering the suspension and drying the precipitated silica.

The separation performed in the preparation process according to the invention usually comprises a filtration, followed by washing, if necessary. The filtration is performed according to any suitable method, for example by means of a belt filter, a rotary filter, for example a vacuum filter, or, preferably a filter press.

The filter cake is then subjected to a liquefaction operation. The term "liquefaction" is intended herein to indicate a process wherein a solid, namely the filter cake, is converted into a fluid-like mass. After the liquefaction step the filter cake is in a flowable, fluid-like form and the precipitated silica is in suspension.

The liquefaction step may comprise a mechanical treatment which results in a reduction of the granulometry of the silica in suspension. Said mechanical treatment may be carried out by passing the filter cake through a high shear mixer, a colloidal-type mill or a ball mill. Alternatively, the liquefaction step may be carried out by subjecting the filter cake to a chemical action by addition for instance of an acid or an aluminum compound, for example sodium aluminate. Still alternatively, the liquefaction step may comprises both a mechanical treatment and a chemical action.

The suspension of precipitated silica which is obtained after the liquefaction step is subsequently preferably dried.

Drying may be performed according to means known in the art. Preferably, drying is performed by atomization. To this end, use may be made of any type of suitable atomizer, in particular a turbine, nozzle, liquid pressure or two-fluid spray-dryer.

When the drying operation is performed using a nozzle spray-dryer, the precipitated silica that may then be obtained is usually in the form of substantially spherical beads. After this drying operation, it is optionally possible to perform a step of milling or micronizing on the recovered product; the precipitated silica that may then be obtained is generally in the form of a powder.

When the drying operation is performed using a turbine spray-dryer, the precipitated silica that may then be obtained may be in the form of a powder.

Finally, the dried, milled or micronized product as indicated previously may optionally be subjected to an agglomeration step, which consists, for example, of direct compression, wet granulation (i.e. with use of a binder, such as water, silica suspension, etc.), extrusion or, preferably, dry compacting.

The precipitated silica that may then be obtained via this agglomeration step is generally in the form of granules.

The inventive precipitated silica can be used in a number of applications, such as absorbent for active materials (in particular support for liquids, especially used in food, such as vitamins (vitamin E or choline chloride)), as viscosity modifier, texturizing or anticaking agent, or as additive for toothpaste, concrete or paper.

The inventive silica may be used as catalyst or as catalyst support. An object of the invention is thus a catalyst or a catalyst support comprising, even consisting of, the inventive precipitated silica.

The inventive silica may also be used in the manufacture of thermally insulating materials or in the preparation of resorcinol-formaldehyde/silica composites. The inventive silica may also be conveniently used as absorbent, for instance in the preparation of personal care or baby care products, e.g. diapers.

The inventive precipitated silica finds a particularly advantageous application as filler in polymeric compositions.

Accordingly, a further object of the invention is a composition comprising the inventive silica as above defined and at least one polymer. The phrase "at least one" when referred to the polymer in the composition is used herein to indicate that one or more than one polymer of each type can be present in the composition.

The expression "copolymer" is used herein to refer to polymers comprising recurring units deriving from at least two monomeric units of different nature.

The at least one polymer can be selected among the thermosetting polymers and the thermoplastic polymers. Notable, non-limiting examples of thermosetting polymers include thermosetting resins such as epoxy resins, unsaturated polyester resins, vinyl ester resins, phenolic resins, epoxy acrylate resins, urethane acrylate resins, phenoxy resins, alkyd resins, urethane resins, maleimide resins, and cyanate resins.

Notable, non-limiting examples of suitable thermoplastic polymers include styrene-based polymers such as polystyrene, (meth)acrylic acid ester/styrene copolymers, acrylonitrile/styrene copolymers, styrene/maleic anhydride copolymers, ABS; acrylic polymers such as polymethylmethacrylate; polycarbonates; polyamides; polyesters, such as polyethylene terephthalate and polybutylene terephthalate; polyphenylene ethers; polysulfones; polyaryletherketones; polyphenylene sulfides; thermoplastic polyurethanes; polyolefins such as polyethylene, polypropylene, polybutene, poly-4-methylpentene, ethylene/propylene copolymers, ethylene/α-olefins copolymers; copolymers of α-olefins and various monomers, such as ethylene/vinyl acetate copolymers, ethylene/(meth)acrylic acid ester copolymers, ethylene/maleic anhydride copolymers, ethylene/acrylic acid copolymers; aliphatic polyesters such as polylactic acid, polycaprolactone, and aliphatic glycol/aliphatic dicarboxylic acid copolymers.

The inventive silica may advantageously be employed as reinforcing filler in elastomeric compositions. Accordingly a preferred object of the invention is a composition comprising the inventive silica and one or more elastomers, preferably exhibiting at least one glass transition temperature between −150° C. and +300° C., for example between −150° C. and +20° C.

Notable non-limiting examples of suitable elastomers are diene elastomers. For example, use may be made of elastomers deriving from aliphatic or aromatic monomers, comprising at least one unsaturation such as, in particular, ethylene, propylene, butadiene, isoprene, styrene, acrylonitrile, isobutylene or vinyl acetate, polybutyl acrylate, or their mixtures. Mention may also be made of functionalized elastomers, that is elastomers functionalized by chemical groups positioned along the macromolecular chain and/or at one or more of its ends (for example by functional groups capable of reacting with the surface of the silica), and halogenated polymers. Mention may be made of polyamides, ethylene homo- and copolymer, propylene homo- and copolymer.

Among diene elastomers mention may be made, for example, of polybutadienes (BRs), polyisoprenes (IRs), butadiene copolymers, isoprene copolymers, or their mixtures, and in particular styrene/butadiene copolymers (SBRs, in particular ESBRs (emulsion) or SSBRs (solution)), isoprene/butadiene copolymers (BIRs), isoprene/styrene copolymers (SIRs), isoprene/butadiene/styrene copolymers (SBIRs), ethylene/propylene/diene terpolymers (EPDMs), and also the associated functionalized polymers (exhibiting, for example, pendant polar groups or polar groups at the chain end, which can interact with the silica).

Mention may also be made of natural rubber (NR) and epoxidized natural rubber (ENR).

The polymer compositions can be vulcanized with sulfur or crosslinked, in particular with peroxides or other crosslinking systems (for example diamines or phenolic resins).

In general, the polymer compositions additionally comprise at least one (silica/polymer) coupling agent and/or at least one covering agent; they can also comprise, inter alia, an antioxidant.

Non-limiting examples of suitable coupling agents are for instance "symmetrical" or "unsymmetrical" silane polysulfides; mention may more particularly be made of bis((C1-C4)alkoxyl(C1-C4)alkylsilyl(C1-C4)alkyl) polysulfides (in particular disulfides, trisulfides or tetrasulfides), such as, for example, bis(3-(trimethoxysilyl)propyl) polysulfides or bis (3-(triethoxysilyl)propyl) polysulfides, such as triethoxysilylpropyl tetrasulfide. Mention may also be made of monoethoxydimethylsilylpropyl tetrasulfide. Mention may also be made of silanes comprising masked or free thiol functional groups.

The coupling agent can be grafted beforehand to the polymer. It can also be employed in the free state (that is to say, not grafted beforehand) or grafted at the surface of the silica. It is the same for the optional covering agent.

The coupling agent can optionally be combined with an appropriate "coupling activator", that is to say a compound which, mixed with this coupling agent, increases the effectiveness of the latter.

The proportion by weight of the inventive silica in the polymer composition can vary within a fairly wide range. It normally represents from 10% to 200%, in particular from 20% to 150%, especially from 20% to 80% (for example from 30% to 70%) or from 80% to 120% (for example from 90% to 110%), of the amount of the polymer(s).

The silica according to the invention can advantageously constitute all of the reinforcing inorganic filler and even all of the reinforcing filler of the polymer composition.

The silica of the invention can optionally be combined with at least one other reinforcing filler, for instance a highly dispersible silica, such as Zeosil® 1165MP, Zeosil® 1115MP, Zeosil® Premium 200MP or Zeosil® 1085 GR (commercially available from Solvay), or another reinforcing inorganic filler, such as nanoclays, alumina. Alternatively, the silica of the invention may be combined with an organic reinforcing filler, such as carbon black nanotubes, graphene and the like.

The silica according to the invention then preferably constitutes at least 40% by weight, indeed even at least 50% by weight, of the total amount of the reinforcing filler.

The compositions comprising the precipitated silica of the invention may be used for the manufacture of a number of articles. Non-limiting examples of finished articles comprising at least one of the polymer compositions described above, are for instance of footwear soles, floor coverings, gas barriers, flame-retardant materials and also engineering components, such as rollers for cableways, seals for domestic electrical appliances, seals for liquid or gas pipes, braking system seals, pipes (flexible), sheathings (in particular cable sheathings), cables, engine supports, battery separators, conveyor belts, or transmission belts.

In a preferred embodiment of the invention the composition comprising the inventive precipitated silica is used for the manufacture of tires or tire components.

Should the disclosure of any patents, patent applications, and publications which are incorporated herein by reference conflict with the description of the present application to the extent that it may render a term unclear, the present description shall take precedence.

Analytical Methods

The physicochemical properties of the precipitated silica of the invention were determined using the methods described hereafter.

Determination of CTAB Surface Area

CTAB surface area ($S_{CTAB}$) values were determined according to standard NF ISO 5794-1, Appendix G.

Determination of BET Surface Area

BET surface area ($S_{BET}$) was determined according to the Brunauer-Emmett-Teller method as detailed in standard NF ISO 5794-1, Appendix E (June 2010) with the following adjustments: the sample was pre-dried at 160° C.±10° C.; the partial pressure used for the measurement $P/P^0$ was between 0.05 and 0.2.

Determination of the Particle Size Distribution and Particle Size by Centrifugal Sedimentation in a Disc Centrifuge (CPS)

Values of d50, d16, d84 and Ld were determined centrifugal sedimentation in a disc centrifuge using a centrifugal photosedimentometer type "CPS DC 24000UHR", marketed by CPS Instruments company. This instrument is equipped with operating software supplied with the device (operating software version 11g).

Instruments used: for the measurement requirement, the following materials and products were used: Ultrasound system: 1500 W generator type Sonics Vibracell VC1500/VCX1500 equipped with 19 mm probe (Converters: CV154+ Boosters (Part No: BHNVC21)+19 mm Probe (Part No: 630-0208)).

Analytical balance with a precision of 0.1 mg (e.g. Mettler AE260); Syringes: 1.0 mL and 2.0 mL with 20 ga needles; high shape glass beaker of 50 mL (SCHOTT DURAN: 38 mm diameter, 78 mm high); magnetic stirrer with a stir bar of 2 cm; vessel for ice bath during sonication.

Chemicals: deionized water; ethanol 96%; sucrose 99%; dodecane, all from Merck; PVC reference standard from CPS Instrument Inc.; the peak maximum of the reference standard used should be between 200 and 600 nm (e.g. 237 nm).

Preparation of the Disc Centrifuge

For the measurements, the following parameters were established. For the calibration standard parameters, the information of the PVC reference communicated by the supplier were used.

| Sample Parameters | | |
|---|---|---|
| max. diameter | μm | 0.79 |
| min. diameter | μm | 0.02 |
| particle density | g/mL | 2.11 |
| particle refrative index | | 1.46 |
| particle absorption | K | 0.001 |
| non-sphericity factor | | 1 |

| Calibration Standard Parameters | | |
|---|---|---|
| peak diameter | nm | 237 |
| half height peak width | μm | 0.023 |
| particle density | | 1.385 |
| Fluid Parameters | | |
| fluid density | g/mL | 1.051 |
| fluid Refractive Index | | 1.3612 |
| fluid viscosity | cps* | 1.28 |

*cps = centipoise

System Configuration

The measurement wavelength was set to 405 nm. The following runtime options parameters were established:

| | |
|---|---|
| Force Baseline: | Yes |
| Correct for Non-Stokes: | No |
| Extra Software Noise Filtration: | No |
| Baseline Drift Display: | Show |
| Calibration method: | External |
| Samples per calibration: | 1 |

All the others options of the software are left as set by the manufacturer of the instrument.

Preparation of the Disc Centrifuge

The centrifugal disc is rotated at 24000 rpm during 30 min. The density gradient of sucrose (CAS no 57-50-1) is prepared as follows:

In a 50 mL beaker, a 24% in weight aqueous solution of sucrose is prepared. In a 50 mL beaker, a 8% in weight aqueous solution of sucrose is prepared. Once these two solutions are homogenized separately, samples are taken from each solution using a 2 mL syringe which is injected into the rotating disc in the following order:

Sample 1: 1.8 mL of the 24 wt % solution
Sample 2: 1.6 mL of the 24 wt % solution+0.2 mL of the 8 wt % solution
Sample 3: 1.4 mL of the 24 wt % solution+0.4 mL of the 8 wt % solution
Sample 4: 1.2 mL of the 24 wt % solution+0.6 mL of the 8 wt % solution
Sample 5: 1.0 mL of the 24 wt % solution+0.8 mL of the 8 wt % solution
Sample 6: 0.8 mL of the 24 wt % solution+1.0 mL of the 8 wt % solution
Sample 7: 0.6 mL of the 24 wt % solution+1.2 mL of the 8 wt % solution
Sample 8: 0.4 mL of the 24 wt % solution+1.4 mL of the 8 wt % solution
Sample 9: 0.2 mL of the 24 wt % solution+1.6 mL of the 8 wt % solution
Sample 10: 1.8 mL of the 8 wt % solution Before each injection into the disk, the two solutions are homogenized in the syringe by aspiring about 0.2 mL of air followed by brief manual agitation for a few seconds, making sure not to lose any liquid.

These injections, the total volume of which is 18 mL, aim to create a density gradient useful for eliminating certain instabilities which may appear during the injection of the sample to be measured. To protect the density gradient from evaporation, we add 1 mL of dodecane in the rotating disc using a 2 mL syringe. The disc is then left in rotation at 24000 rpm for 60 min before any first measurement.

Sample Preparation 3.2 g of silica in a 50 mL high shape glass beaker (SCHOTT DURAN: diameter 38 mm, height 78 mm) were weighed and 40 mL of deionized water were added to obtain a 8 wt % suspension of silica. The suspension was stirred with a magnetic stirrer (minimum 20 s) before placing the beaker into a crystallizing dish filled with ice and cold water. The magnetic stirrer was removed and the crystallizing dish was placed under the ultrasonic probe placed at 1 cm from the bottom of the beaker. The ultrasonic probe was set to 56% of its maximum amplitude and was activated for 8 min. At the end of the sonication the beaker was placed again on the magnetic stirrer with a 2 cm magnetic stir bar stirring at minimum 500 rpm until after the sampling.

The ultrasonic probe should be in proper working conditions. The following checks have to be carried out and in case of negative results a new probe should be used: visual check of the physical integrity of the end of the probe (depth of roughness less than 2 mm measured with a fine caliper); the measured d50 of commercial silica Zeosil® 1165MP should be 93 nm±3 nm.

Analysis

Before each samples was analysed, a calibration standard was recorded. In each case 0.1 mL of the PVC standard provided by CPS Instruments and whose characteristics were previously entered into the software was injected. It is important to start the measurement in the software simultaneously with this first injection of the PVC standard. The confirmation of the device has to be received before injecting 100 µL of the previously sonicated sample by making sure that the measurement is started simultaneously at the injection.

These injections were done with 2 clean syringes of 1 mL.

At the end of the measurement, which is reached at the end of the time necessary to sediment all the particles of smaller diameter (configured in the software at 0.02 µm), the ratio for each diameter class was obtained. The curve obtained is called aggregate size distribution.

Results

The values d50, d16, d84 and Ld are on the basis of distributions drawn in a linear scale. The integration of the particle size distribution function of the diameter allows obtaining a "cumulative" distribution, that is to say the total mass of particles between the minimum diameter and the diameter of interest.

d50: is the diameter below and above which 50% of the population by mass is found. The d50 is called median size, that is diameter, of the silica particle.

d84: is the diameter below which 84% of the total mass of particles is measured.

d16: is the diameter below which 16% of the total mass of particles is measured.

Ld: is calculated according to equation: Ld=(d84−d16)/d50

Determination of Content of Metal M

The content of metal M can be determined by means of ICP OES (inductively coupled plasma optical emission spectrometry) using commonly know procedures.

The determination of Ti and Zr was made after digestion of the sample in fluorhydric acid (eg. 0.2-0.3 g of $SiO_2$ with 1 mL of fluorhydric acid 40%). The limpid solution was diluted in a 5% nitric acid aqueous solution according to the expected Zr and Ti concentration. The intensity measured on the Zr specific wavelengths (343.823 and 267.863 nm) and Ti specific wavelengths (336.122 nm) were compared to a calibration curve in the range of 0.05 to 2.00 mg/L obtained using Zr and Ti standards (4 standards at 0.10, 0.20, 1.00 and 2.00 mg/L) in similar analytical conditions. The amount in the solid was obtained by calculation using the dilution factor and the dry extract of the silica measured.

The content of Y was determined after extraction of the sample in nitric acid (eg. 0.5 g of $SiO_2$ with 10 mL of nitric acid 85%). After addition and mixing during 30 minutes, the solid suspension was diluted by addition of ultrapure water to 50 mL. The suspension of silica in diluted nitric acid solution was then mixed over a period of 30 minutes. After 30 minutes, the supernatant was filtered using a 0.45 µm PVDF syringe filter. The limpid solution obtained was diluted in a 5% nitric acid aqueous solution according to the expected Y concentration. The intensity measured on the Y specific wavelengths (412.831, 324.228 and 371.030 nm) was compared to a calibration curve in the range of 0.05 to 2.00 mg/L obtained using Y standards (4 standards at 0.10, 0.20, 1.00 and 2.00 mg/L) in similar analytical conditions. The amount in the solid was obtained by calculation using the dilution factor and the dry extract of the silica measured.

EXAMPLES

Example 1

In a 25 L stainless steel reactor were introduced 167 L of purified water and 260 g of $Na_2SO_4$ (solid). The obtained solution was stirred and heated to reach 92° C. The entire reaction was carried out at this temperature and under stirring to maintain a homogeneous reaction medium. Sulfuric acid (concentration: 7.7 wt %) was introduced into the reactor to reach a pH value of 3.90.

A sodium silicate solution ($SiO_2/Na_2O$ weight ratio=3.4; $SiO_2$ concentration=19.3 wt %) at a flowrate of 111 g/min was introduced in the reactor over a period of 45 s. The same sodium silicate solution was used throughout the process. Next a sodium silicate solution at a flowrate of 111 g/min and a 7.7 wt % sulfuric acid solution at a flowrate of 190 g/min were simultaneously introduced over a 2 min period. The flowrate of sulfuric acid was regulated so that the pH of the reaction medium was maintained at a value of 3.95 with a sodium silicate flowrate of 111 g/min. At the end of this step, sodium silicate at a flowrate of 111 g/min and a 96 wt % sulfuric acid solution were introduced simultaneously over a period of 10 min. The flowrate of the 96 wt % sulfuric acid solution was regulated so that the pH of the reaction medium was maintained at a value of 3.95.

The introduction of acid was then stopped while the addition of sodium silicate was maintained at the same flowrate until the reaction medium reached the pH value of 8.00.

Sodium silicate at a flowrate of 178 g/min and a 96 wt % sulfuric acid solution were then introduced simultaneously over a period of 3 min. The flowrate of the 96 wt % sulfuric acid solution was regulated so that the pH of the reaction medium was maintained at a value of 8.00.

Simultaneously, over a period of 15 min, were introduced: sodium silicate, at a flowrate of 178 g/min, a titanium oxysulfate solution ([$TiOSO_4$]: 15 wt %), at a flowrate of 17.3 g/min, and a 96 wt % sulfuric acid solution. The flowrate of the 96 wt % sulfuric acid solution was regulated so that the pH of the reaction medium was maintained at a value of 8.00.

At the end of this simultaneous addition, the pH of the reaction medium was brought to a value of 4.80 with 96 wt % sulfuric acid. The reaction mixture was matured for 5 minutes. A slurry was obtained.

The reaction slurry was filtered and washed on a press filter. The cake obtained was disintegrated mechanically. The resulting slurry was dried by means of a nozzle spray dryer to obtain precipitated silica S1. The properties of precipitated silica S1 are reported in Table 2.

Example 2

In a 25 L stainless steel reactor were introduced 167 L of purified water and 260 g of $Na_2SO_4$ (solid). The obtained solution was stirred and heated to reach 92° C. The entire reaction was carried out at this temperature and under stirring to maintain a homogeneous reaction medium. Sulfuric acid (concentration: 7.7 wt %) was introduced into the reactor to reach a pH value of 3.90.

A sodium silicate solution ($SiO_2/Na_2O$ weight ratio=3.4; $SiO_2$ concentration=19.3 wt %) at a flowrate of 111 g/min was introduced in the reactor over a period of 45 s. The same sodium silicate solution was used throughout the process. Next a sodium silicate solution at a flowrate of 111 g/min and a 7.7 wt % sulfuric acid solution at a flowrate of 190 g/min were simultaneously introduced over a 2 min period. The flowrate of sulfuric acid was regulated so that the pH of the reaction medium was maintained at a value of 3.95 with a sodium silicate flowrate of 111 g/min. At the end of this step, sodium silicate at a flowrate of 111 g/min and a 96 wt % sulfuric acid solution were introduced simultaneously over a period of 10 min. The flowrate of the 96 wt % sulfuric acid solution was regulated so that the pH of the reaction medium was maintained at a value of 3.95.

The introduction of acid was then stopped while the addition of sodium silicate was maintained at the same flowrate until the reaction medium reached the pH value of 8.00.

Sodium silicate at a flowrate of 178 g/min and a 96 wt % sulfuric acid solution were then introduced simultaneously over a period of 3 min. The flowrate of the 96 wt % sulfuric acid solution was regulated so that the pH of the reaction medium was maintained at a value of 8.00.

Simultaneously, over a period of 15 min, were introduced: sodium silicate, at a flowrate of 178 g/min, a zirconium sulfate solution ($[Zr(SO_4)_2, 4H_2O]$: 23.6 wt %), at a flowrate of 12.3 g/min, and a 96 wt % sulfuric acid solution. The flowrate of the 96 wt % sulfuric acid solution was regulated so that the pH of the reaction medium was maintained at a value of 8.00.

At the end of this simultaneous addition, the pH of the reaction medium was brought to a value of 4.80 with 96 wt % sulfuric acid. The reaction mixture was matured for 5 minutes. A slurry was obtained.

The reaction slurry was filtered and washed on a press filter. The cake obtained was disintegrated mechanically. The resulting slurry was dried by means of a nozzle spray dryer to obtain precipitated silica S2. The properties of precipitated silica S2 are reported in Table 2.

Example 3

In a 25 L stainless steel reactor were introduced 167 L of purified water and 260 g of $Na_2SO_4$ (solid). The obtained solution was stirred and heated to reach 92° C. The entire reaction was carried out at this temperature and under stirring to maintain a homogeneous reaction medium. Sulfuric acid (concentration: 7.7 wt %) was introduced into the reactor to reach a pH value of 3.90.

A sodium silicate solution ($SiO_2/Na_2O$ weight ratio=3.4; $SiO_2$ concentration=19.3 wt %) at a flowrate of 111 g/min was introduced in the reactor over a period of 45 s. The same sodium silicate solution was used throughout the process. Next a sodium silicate solution at a flowrate of 111 g/min and a 7.7 wt % sulfuric acid solution at a flowrate of 190 g/min were simultaneously introduced over a 2 min period. The flowrate of sulfuric acid was regulated so that the pH of the reaction medium was maintained at a value of 3.95 with a sodium silicate flowrate of 111 g/min. At the end of this step, sodium silicate at a flowrate of 111 g/min and a 96 wt % sulfuric acid solution were introduced simultaneously over a period of 10 min. The flowrate of the 96 wt % sulfuric acid solution was regulated so that the pH of the reaction medium was maintained at a value of 3.95.

The introduction of acid was then stopped while the addition of sodium silicate was maintained at the same flowrate until the reaction medium reached the pH value of 8.00.

Sodium silicate at a flowrate of 178 g/min and a 96 wt % sulfuric acid solution were then introduced simultaneously over a period of 3 min. The flowrate of the 96 wt % sulfuric acid solution was regulated so that the pH of the reaction medium was maintained at a value of 8.00.

Simultaneously, over a period of 15 min, were introduced: sodium silicate, at a flowrate of 178 g/min, a zirconium sulfate solution ($[Zr(SO_4)_2, 4H_2O]$: 23.6 wt %), at a flowrate of 24.7 g/min, and a 96 wt % sulfuric acid solution. The flowrate of the 96 wt % sulfuric acid solution was regulated so that the pH of the reaction medium was maintained at a value of 8.00.

At the end of this simultaneous addition, the pH of the reaction medium was brought to a value of 4.80 with 96 wt % sulfuric acid. The reaction mixture was matured for 5 minutes. A slurry was obtained.

The reaction slurry was filtered and washed on a press filter. The cake obtained was disintegrated mechanically. The resulting slurry was dried by means of a nozzle spray dryer to obtain precipitated silica S3. The properties of precipitated silica S3 are reported in Table 2.

Example 4

In a 25 L stainless steel reactor were introduced 167 L of purified water and 260 g of $Na_2SO_4$ (solid). The obtained solution was stirred and heated to reach 92° C. The entire reaction was carried out at this temperature and under stirring to maintain a homogeneous reaction medium. Sulfuric acid (concentration: 7.7 wt %) was introduced into the reactor to reach a pH value of 3.90.

A sodium silicate solution ($SiO_2/Na_2O$ weight ratio=3.4; $SiO_2$ concentration=19.3 wt %) at a flowrate of 111 g/min was introduced in the reactor over a period of 45 s. The same sodium silicate solution was used throughout the process. Next a sodium silicate solution at a flowrate of 111 g/min and a 7.7 wt % sulfuric acid solution at a flowrate of 190 g/min were simultaneously introduced over a 2 min period. The flowrate of sulfuric acid was regulated so that the pH of the reaction medium was maintained at a value of 3.95 with a sodium silicate flowrate of 111 g/min. At the end of this step, sodium silicate at a flowrate of 111 g/min and a 96 wt % sulfuric acid solution were introduced simultaneously over a period of 10 min. The flowrate of the 96 wt % sulfuric acid solution was regulated so that the pH of the reaction medium was maintained at a value of 3.95.

The introduction of acid was then stopped while the addition of sodium silicate was maintained at the same flowrate until the reaction medium reached the pH value of 8.00.

Sodium silicate at a flowrate of 178 g/min and a 96 wt % sulfuric acid solution were then introduced simultaneously over a period of 3 min. The flowrate of the 96 wt % sulfuric acid solution was regulated so that the pH of the reaction medium was maintained at a value of 8.00.

Simultaneously, over a period of 15 min, were introduced: sodium silicate, at a flowrate of 178 g/min, a zirconium sulfate solution ($[Zr(SO_4)_2, 4H_2O]$: 23.6 wt %), at a flowrate of 36.6 g/min, and a 96 wt % sulfuric acid solution. The flowrate of the 96 wt % sulfuric acid solution was regulated so that the pH of the reaction medium was maintained at a value of 8.00.

At the end of this simultaneous addition, the pH of the reaction medium was brought to a value of 4.80 with 96 wt % sulfuric acid. The reaction mixture was matured for 5 minutes. A slurry was obtained.

The reaction slurry was filtered and washed on a press filter. The cake obtained was disintegrated mechanically. The resulting slurry was dried by means of a nozzle spray dryer to obtain precipitated silica S4. The properties of precipitated silica S4 are reported in Table 2.

Example 5

In a 25 L stainless steel reactor were introduced 167 L of purified water and 260 g of $Na_2SO_4$ (solid). The obtained solution was stirred and heated to reach 92° C. The entire reaction was carried out at this temperature and under stirring to maintain a homogeneous reaction medium. Sulfuric acid (concentration: 7.7 wt %) was introduced into the reactor to reach a pH value of 3.90.

A sodium silicate solution ($SiO_2/Na_2O$ weight ratio=3.4; $SiO_2$ concentration=19.3 wt %) at a flowrate of 111 g/min was introduced in the reactor over a period of 45 s. The same sodium silicate solution was used throughout the process. Next a sodium silicate solution at a flowrate of 111 g/min and a 7.7 wt % sulfuric acid solution at a flowrate of 190 g/min were simultaneously introduced over a 2 min period. The flowrate of sulfuric acid was regulated so that the pH of the reaction medium was maintained at a value of 3.95 with a sodium silicate flowrate of 111 g/min. At the end of this step, sodium silicate at a flowrate of 111 g/min and a 96 wt % sulfuric acid solution were introduced simultaneously over a period of 10 min. The flowrate of the 96 wt % sulfuric acid solution was regulated so that the pH of the reaction medium was maintained at a value of 3.95.

The introduction of acid was then stopped while the addition of sodium silicate was maintained at the same flowrate until the reaction medium reached the pH value of 8.00.

Sodium silicate at a flowrate of 178 g/min and a 96 wt % sulfuric acid solution were then introduced simultaneously over a period of 3 min. The flowrate of the 96 wt % sulfuric acid solution was regulated so that the pH of the reaction medium was maintained at a value of 8.00.

Simultaneously, over a period of 15 min, were introduced: sodium silicate, at a flowrate of 178 g/min, a yttrium sulfate solution ($[Y_2(SO_4)_3, 8H_2O]$: 5.52 wt %), at a flowrate of 90.5 g/min, and a 96 wt % sulfuric acid solution. The flowrate of the 96 wt % sulfuric acid solution was regulated so that the pH of the reaction medium was maintained at a value of 8.00.

At the end of this simultaneous addition, the pH of the reaction medium was brought to a value of 4.80 with 96 wt % sulfuric acid. The reaction mixture was matured for 5 minutes. A slurry was obtained.

The reaction slurry was filtered and washed on a press filter. The cake obtained was disintegrated mechanically. The resulting slurry was dried by means of a nozzle spray dryer to obtain precipitated silica S5. The properties of precipitated silica S5 are reported in Table 2.

Comparative Example 1

Example 8 in FR2997405 is reproduced starting from a filter cake of Zeosil® 1165 MP (commercially available from Solvay SA). The properties of precipitated silica CS1 are reported in Table 2.

TABLE 2

| Silica | M | $S_{CTAB}$ ($m^2/g$) | $S_{BET}$ ($m^2/g$) | d50 (CPS) (nm) | $W_M$ (mol %) |
|---|---|---|---|---|---|
| S1 | Ti | 218 | 264 | 117 | 1.2 |
| S2 | Zr | 224 | 264 | 113 | 0.6 |
| S3 | Zr | 221 | 272 | 122 | 1.2 |
| S4 | Zr | 230 | 286 | 115 | 1.8 |
| S5 | Y | 224 | 262 | 112 | 0.5 |
| CS1 | Ti | 157 | 167 | 90 | 1.4 |

Example 6 and 7

Comparative Example 2

Silica-filled elastomeric compositions were prepared. The compositions, expressed as parts by weight per 100 parts of elastomers (phr), are described in Table 3.

TABLE 3

| Composition | Example 6 | Example 7 | Comp. Example 1 |
|---|---|---|---|
| sSBR (1) | 110.0 | 110.0 | 110.0 |
| BR (2) | 20.0 | 20.0 | 20.0 |
| Silica CS2 (3) | | | 80.0 |
| Silica S2 | 80.0 | | |
| Silica S4 | | 80.0 | |
| Carbon black (N234) | 3.0 | 3.0 | 3.0 |
| TESPT (4) | 8.8 | 9.2 | 8.0 |
| Stearic acid | 2.0 | 2.0 | 2.0 |
| 6-PPD (5) | 2.5 | 2.5 | 2.5 |
| ZnO | 1.2 | 1.2 | 1.2 |
| DPG (6) | 2.5 | 2.7 | 1.9 |
| Resin (7) | 20.0 | 20.0 | 20.0 |
| Sulfur | 1.0 | 1.0 | 1.0 |
| CBS (8) | 2.3 | 2.3 | 2.3 |

(1) Oil extended solution SBR, Buna VSL4526-2HM from Lanxess with 45% of vinyl units; 26% of styrene units; Tg of −30° C., 37.5 phr of TDAE
(2) BR, Buna CB 25 from Lanxess
(3) Silica CS2: Zeosil ® Premium 200MP from Solvay: $S_{CTAB}$ 197 $m^2/g$; $S_{BET}$ 219 $m^2/g$; d50 (CPS) 99 nm
(4) Bis[3-(triethoxysilyl)propyl] Tetrasulfide, TESPT Luvomaxx, from LEVOSS France sarl
(5) N-(1,3-Dimethylbutyl)-N-phenyl-para-phenylenediamine, Santoflex 6-PPD from Flexsys
(6) Diphenylguanidine, Rhenogran DPG-80 from RheinChemie
(7) Polyterpene resin Sylvares TR 5147 from ARIZONA CHEMICAL
(8) N-Cyclohexyl-2-benzothiazolesulfenamide, Rhenogran CBS-80 from Rhein Chemie The process for the preparation of the rubber compositions was carried out in two successive preparation phases: a first phase of high-temperature thermomechanical working, followed by a second phase of mechanical working at temperatures of less than 110° C. to introduce the vulcanization system.

The first phase was carried out using a mixing device, of internal mixer type, of Brabender brand (capacity of 380 mL). The initial temperature and the speed of the rotors were set so as to achieve mixture dropping temperatures of approximately 162° C.

During the first phase the elastomers and the reinforcing filler (introduction in installments) were mixed with the coupling agent and the other additives (DPG, stearic acid, resin, ZnO, 6-PPD). The duration of this phase was around 6 min.

After cooling the mixture (temperature of less than 110° C.), the vulcanization system was added during the second phase. This phase was carried out on an open mill, preheated to 50° C. The duration of this phase was between 2 and 6 minutes. Each final mixture was subsequently calendared in the form of plaques with a thickness of 2-3 mm.

Mechanical Properties of the Vulcanisates

The measurements were carried out after vulcanization at 150° C.

Uniaxial tensile tests were carried out in accordance with the instructions of standard NF ISO 37 with test specimens of H2 type at a rate of 500 mm/min on an Instron 5564 device. The x % moduli, corresponding to the stress measured at x % of tensile strain, are expressed in MPa.

The measurement of the loss of mass by abrasion was performed according to the indications of standard DIN 53516, using a Montech abrasimeter in which the cylindrical specimen is subjected to the action of an abrasive gauze of P60 grains and attached to the surface of a rotating drum at a contact pressure of 10 N and over a course of 40 meters. The value measured is a volume of loss of substance (in $mm^3$) after abrasion wear; the smaller the value, the better the abrasion resistance.

The values of the loss factor (tan δ) and amplitude of elastic modulus in dynamic shear (ΔG') were recorded on vulcanized samples (parallelepipedal specimen of cross section 8 $mm^2$ and of height 7 mm). The sample was subjected to a double alternating sinusoidal shear strain at a temperature of 40° C. and at a frequency of 10 Hz. The strain amplitude sweeping processes were performed according to an outward-return cycle, proceeding outward from 0.1% to 50% and then returning from 50% to 0.1%. The values reported in Table 4 were obtained from the return strain amplitude scanning and concern the maximum value of the loss factor (tan δ max) and the amplitude of the elastic modulus (ΔG') between the values at 0.1% and 50% of strain (Payne effect).

TABLE 4

|  | Example 6 | Example 7 | Comp. Example 2 |
| --- | --- | --- | --- |
| 100% Modulus (MPa) | 2.1 | 2.3 | 2.1 |
| 300% Modulus (MPa) | 10.0 | 10.1 | 9.2 |
| Abrasion loss ($mm^3$) | 125 | 121 | 130 |
| ΔG' (MPa) | 2.13 | 1.56 | 2.43 |
| tan δ max | 0.269 | 0.238 | 0.281 |

The compositions of Example 6 and 7 containing the inventive silica exhibit significantly reduced energy dissipation values (ΔG' and tan δ max), better wear resistance and good mechanical properties with respect to the composition containing a precipitated silica according to the prior art.

The invention claimed is:

1. A precipitated silica comprising:
    a CTAB surface area $S_{CTAB}$ in the range from 70 to 350 $m^2/g$;
    an amount $W_M$ of at least one metal M selected from the group consisting of the elements of groups 3, 4 and 5 of at least 0.1 mol %; and
    a median particle size d50, measured by centrifugal sedimentation, such that (I):

$$|d50| \geq 183 \times |R_{ION}| \times |W_M| - 0.67 \times |S_{CTAB}| + 233 \quad (I)$$

wherein:
    |d50| represents the numerical value of the median particle size d50 measured by centrifugal sedimentation and expressed in nm; $|R_{ION}|$ represents the numerical value of the ionic radius of the at least one metal M selected from the group consisting of the elements of groups 3, 4, and 5 expressed in nm; $|S_{CTAB}|$ represents the numerical value of the CTAB surface area $S_{CTAB}$ expressed in $m^2/g$; and $|W_M|$ represents the numerical value of the percentage molar amount of the metal $W_M$,
    wherein the width of the particle size distribution Ld, measured by centrifugal sedimentation, is from 1.2 to 3.5.

2. The precipitated silica according to claim 1, wherein the CTAB surface area $S_{CTAB}$ is in the range from 80 to 300 $m^2/g$.

3. The precipitated silica according to claim 1, wherein the amount of the at least one metal M, $W_M$, is in the range from 0.1 to 7.0 mol %.

4. The precipitated silica according to claim 1, wherein the metal M is selected from the group consisting of Sc, Y, Ti, Zr and Hf.

5. The precipitated silica according to claim 1, wherein the width of the particle size distribution Ld, measured by centrifugal sedimentation, is from 1.4 to 3.0.

6. The precipitated silica according to claim 1, wherein the width of the particle size distribution Ld, measured by centrifugal sedimentation, is from 1.5 to 2.8.

7. The precipitated silica according to claim 1, wherein the width of the particle size distribution Ld, measured by centrifugal sedimentation, is from 1.6 to 2.5.

8. The precipitated silica according to claim 1, wherein the metal M is selected from the group consisting of Y, Ti and Zr.

9. The precipitated silica according to claim 1, wherein the metal M is Zr.

10. The precipitated silica according to claim 1, wherein the CTAB surface area $S_{CTAB}$ is in the range from 130 to 280 $m^2/g$.

11. A composition comprising the precipitated silica of claim 1 and at least one polymer.

12. The composition of claim 11, wherein the at least one polymer is selected from the group of elastomers.

13. An article comprising the precipitated silica of claim 1.

14. The article of claim 13 is in the form of footwear sole, floor covering, gas barrier, rollers for cableways, seal for domestic electrical appliances, seals for liquid or gas pipes, braking system seal, pipes, sheathings, cables, engine support, battery separator, conveyor belt, or transmission belt.

15. A tire or tire component comprising the precipitated silica of claim 1.

16. A catalyst, catalyst support, or personal care or baby care product comprising the precipitated silica of claim 1.

* * * * *